United States Patent [19]
Kodaira et al.

[11] 4,283,344
[45] Aug. 11, 1981

[54] PROCESS FOR PRODUCING 1,1,3,3-TETRAFLUORO-1,3-DIHYDRO-ISOBENZOFURAN

[75] Inventors: Tsumoru Kodaira, Takatsuki; Yoshiro Kobayashi, Tokyo; Hitoshi Kurono, Toyonaka, all of Japan

[73] Assignee: Nihon Nohyaku Co., Ltd., Tokyo, Japan

[21] Appl. No.: 128,190

[22] Filed: Mar. 7, 1980

[30] Foreign Application Priority Data

Mar. 9, 1979 [JP] Japan .................................. 54-27312

[51] Int. Cl.$^3$ ........................................... C07D 307/78
[52] U.S. Cl. ............................................... 260/346.22
[58] Field of Search ................................... 260/346.22

[56] References Cited

PUBLICATIONS

Chem. Abstracts; 55, 19888h (1961).

*Primary Examiner*—Henry R. Jiles
*Assistant Examiner*—Bernard Dentz
*Attorney, Agent, or Firm*—Cushman, Darby & Cushman

[57] ABSTRACT

1,1,3,3-Tetrafluoro-1,3-dihydro-isobenzofuran is produced easily in good yield and high purity by allowing $\alpha,\alpha,\alpha$-trichloro-o-toluic chloride to react with anhydrous hydrogen fluoride at an amount ratio of 4 moles or slight excess of the latter to 1 mole of the former. The final product may be used as an intermediate in the preparation of a fungicidal compound.

2 Claims, No Drawings

PROCESS FOR PRODUCING 1,1,3,3-TETRAFLUORO-1,3-DIHYDRO-ISOBENZOFURAN

This invention relates to a new process for producing 1,1,3,3-tetrafluoro-1,3-dihydro-isobenzofuran.

As process for synthesizing 1,1,3,3-tetrafluoro-1,3-dihydro-isobenzofuran [compound (I)], a method by reaction of 1,1,3,3-tetrachloro-1,3-dihydro-isobenzofuran with antimony trifluoride has been known (Chemical Abstracts, 55, 19888h (1961)). This reaction can be represented diagramatically as follows:

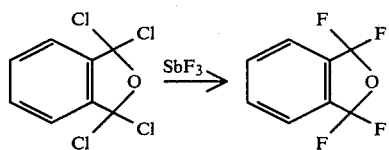

This process incidentally produces $\alpha,\alpha,\alpha$-trifluoro-o-toluic fluoride, has difficulty in separation and recovery of compound (I) by distillation, and additionally, the yield is low; and thus, this process can hardly be said as an industrial process.

The object of the present invention is to provide an industrial process for producing 1,1,3,3-tetrafluoro-1,3-dihydro-isobenzofuran.

According to this invention, there is provided a process for producing 1,1,3,3-tetrafluoro-1,3-dihydroisobenzofuran, which is characterized by reacting $\alpha,\alpha,\alpha$-trichloro-o-toluic chloride with anhydrous hydrogen fluoride at an amount ratio of 4 moles or slight excess of the latter to 1 mole of the former.

The process of this invention can be represented diagramatically as follows:

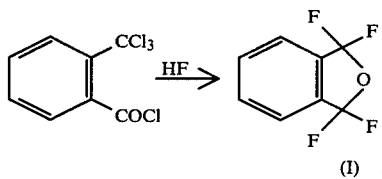

According to the process of this invention, compound (I) can be synthesized in good yield.

The amount of anhydrous hydrogen fluoride used is recommended to decide properly within the range of its amount ratio from 4 moles to a slight excess per 1 mole of $\alpha,\alpha,\alpha$-trichloro-o-toluic chloride. The use of the larger amount of anhydrous hydrogen fluoride is undesirable, because no improved yield can be expected and it rather causes formation of the by-product, $\alpha,\alpha,\alpha$-trifluoro-o-toluic fluoride, which is difficult to separate by distillation. It is to be understood that the word "a slight excess" used in this specification means for the purpose an amount range which exceeds the stoichiometric quantity to the extent acceptable in the common sense on the processing of chemical reaction. Accordingly, an excess of about 10% of the stoichiometric quantity is included within the range of "a slight excess" mentioned in this invention; for example, it is a proper case to use 4 to 4.4 moles of anhydrous hydrogen fluoride per 1 mole of $\alpha,\alpha,\alpha$-trichloro-o-toluic chloride. Unlike this, the use of anhydrous hydrogen fluoride in an excess of 20% over the stoichiometric quantity is undesirable, because it results in contamination with 5 to 10% of the by-product.

For operating the process of this invention, it is recommended that $\alpha,\alpha,\alpha$-trichloro-o-toluic chloride and anhydrous hydrogen fluoride are placed into a pressure and corrosion-resistant vessel and heated to react under sealed condition. The reaction temperature may be properly selected within the range of 50° to 150° C., and particularly the range of about 90° to 120° C. is preferable. The reaction is completed within 1 to 5 hours.

After the reaction is completed, on separation from the reaction mixture according to ordinary way the object compound can be obtained as a liquid having a boiling point of 154° to 156° C. and a purity of 97% or more, in a yield of 90% or more. The compound (I) is useful as a intermediate for synthesis of useful organic compounds, and particularly for agricultural and horticultural fungicide.

EXAMPLE 1

Into a Hastelloy autoclave 15 g (0.057 mole) of $\alpha,\alpha,\alpha$-trichloro-o-toluic chloride was placed and 5 g (0.25 mole) of anhydrous hydrogen fluoride was added. The mixture was heated with an oil bath, stirred and reacted at 90°–120° C. for 3.5 hours. After left to cool down to room temperature, the autoclave was cooled with ice-cold water to draw out gaseous hydrogen chloride formed by the reaction, and the autoclave was opened to feed a small amount of sodium fluoride. Into a polyethylene flask in which a mixture of ice and sodium hydrogen carbonate had been placed, was poured the reaction mixture with the aid of methylene dichloride. Then, the product was extracted with methylene dichloride, thoroughly washed with water, and dried over anhydrous sodium sulfate. After methylene dichloride has been distilled off at atmospheric pressure, the residue was distilled at atmospheric pressure to obtain 10.6 g of 1,1,3,3-tetrafluoro-1,3-dihydroisobenzofuran; b.p. 154°–156° C., yield 95%, purity 97%. A part of the above-mentioned extract from the reaction products was taken off and subjected to gas chromatography to compare with an authentic sample. The results showed no formation of $\alpha,\alpha,\alpha$-trifluoro-o-toluic fluoride. In measurement of $^{19}F$-nuclear magnetic resonance spectrum 1,1,3,3-tetrafluoro-1,3-dihydroisobenzofuran thus obtained gives a signal of +6.4 ppm (S) with $\alpha,\alpha,\alpha$-trifluorotoluene as an internal standard, and in measurement of mass spectrum it gives a molecular ion peak at 192 m/l.

EXAMPLE 2

Into a Hastelloy autoclave 15 g (0.057 mole) of $\alpha,\alpha,\alpha$-trichloro-o-toluic chloride was placed and 5 g (0.25 mole) of anhydrous hydrogen fluoride was added. The mixture was heated to 50° C. with an oil bath, immediately cooled with ice-cold water, and evolved gaseous hydrogen chloride was drawn out. Then, the mixture was stirred and reacted at 90°–120° C. for 3 hours, and thereafter was treated in the same way as in Example 1, giving 10 g of the object compound; yield 90%, purity 97%, b.p. 154°–156° C. The gas chromatography showed no formation of $\alpha,\alpha,\alpha$-trifluoro-o-toluic chloride.

Kodiara et al U.S. application Ser. No. 128,124 shows that Compound (I) may be reacted with anhydrous hydrogen fluoride in a pressure and corrosion resistant vessel and treated at 50° to 150° C. under autogeneous pressure to produce $\alpha,\alpha,\alpha$-trifluorotoluic fluoride. This compound is used to produce o-trifluoromethyl-m-isopropoxybenzoyl anilide. This compound is useful in controlling agricultural and horticultural diseases as shown in U.S. Pat. No. 4,093,743.

We claim:

1. A process for producing 1,1,3,3-tetrafluoro-1,3-dihydro-isobenzofuran, which is characterized by reacting α,α,α-trichloro-o-toluic chloride with anhydrous hydrogen fluoride at an amount ratio of 4 moles or slight excess of the latter to 1 mole of the former.

2. The process according to claim 1, wherein the reaction is carried out at a temperature of 50° to 150° C.

* * * * *